United States Patent [19]
Herrmann

[11] Patent Number: 5,500,075
[45] Date of Patent: Mar. 19, 1996

[54] LEG ELASTIC APPLICATOR WHICH MAINTAINS THE SPACING BETWEEN THE ELASTICS SUBSTANTIALLY CONSTANT

[75] Inventor: Thomas R. Herrmann, Federal Way, Wash.

[73] Assignee: Paragon Trade Brands, Inc., Federal Way, Wash.

[21] Appl. No.: 233,247

[22] Filed: Apr. 26, 1994

[51] Int. Cl.⁶ ............................. A61F 13/15; B32B 31/08
[52] U.S. Cl. ........................ 156/494; 156/161; 156/163; 156/164; 156/229; 604/385.2
[58] Field of Search ........................ 156/494, 495, 156/160–164, 229; 2/400; 604/385.2

[56] References Cited

U.S. PATENT DOCUMENTS

| | | |
|---|---|---|
| 4,507,163 | 3/1985 | Menard . |
| 4,617,082 | 10/1986 | Oshefsky et al. . |
| 4,626,305 | 12/1986 | Suzuki et al. . |
| 4,675,068 | 6/1987 | Lundmark . |
| 4,764,242 | 8/1988 | Gressick et al. . |
| 4,801,345 | 1/1989 | Dussaud et al. . |
| 4,915,767 | 4/1990 | Rajala et al. . |
| 4,917,746 | 4/1990 | Kons et al. . |
| 4,938,821 | 7/1990 | Soderlund et aL. . |
| 4,995,928 | 2/1991 | Sabee . |
| 5,147,487 | 9/1992 | Nomura et al. . |
| 5,209,801 | 5/1993 | Smith . |
| 5,275,676 | 1/1994 | Rooyakkers et al. . |
| 5,389,173 | 2/1995 | Merkatoris et al. .............. 604/385.2 X |

FOREIGN PATENT DOCUMENTS

| | | |
|---|---|---|
| 4-122257 | 4/1992 | Japan . |
| 4-317650 | 11/1992 | Japan . |
| 4-317649 | 11/1992 | Japan . |
| 224838A | 4/1992 | United Kingdom . |
| 89/00189 | 4/1989 | WIPO . |
| 9207531 | 5/1992 | WIPO ................................ 604/385.2 |

*Primary Examiner*—Jeff H. Aftergut
*Attorney, Agent, or Firm*—Klarquist Sparkman Campbell Leigh & Whinston

[57] ABSTRACT

A machine for applying elastic to material is provided that includes a conveyor for carrying material. The conveyor moves the material in one direction along a flow path. An elastic band storage with a plurality of elongate elastic bands is provided for application to the material. An elastic feeder has a feeder head that feeds the plurality of elastic bands directly onto the material while the feeder head moves laterally across the flow path. The lateral movement of the feeder head across the moving conveyor applies the elastic bands to the material in a curved contour. The feeder head is operable to feed the elastic bands onto the material while maintaining a selected spacing between individual elastic bands throughout the curved contour.

28 Claims, 14 Drawing Sheets

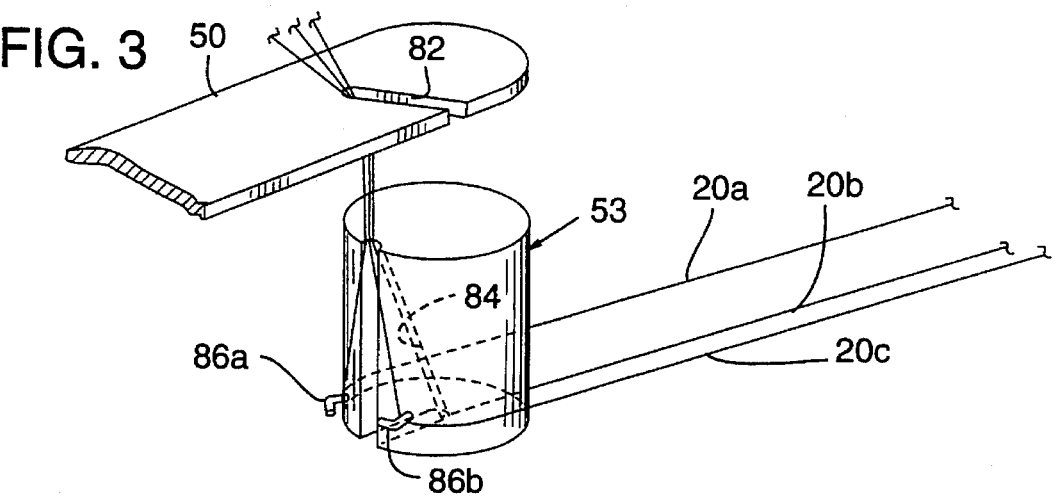
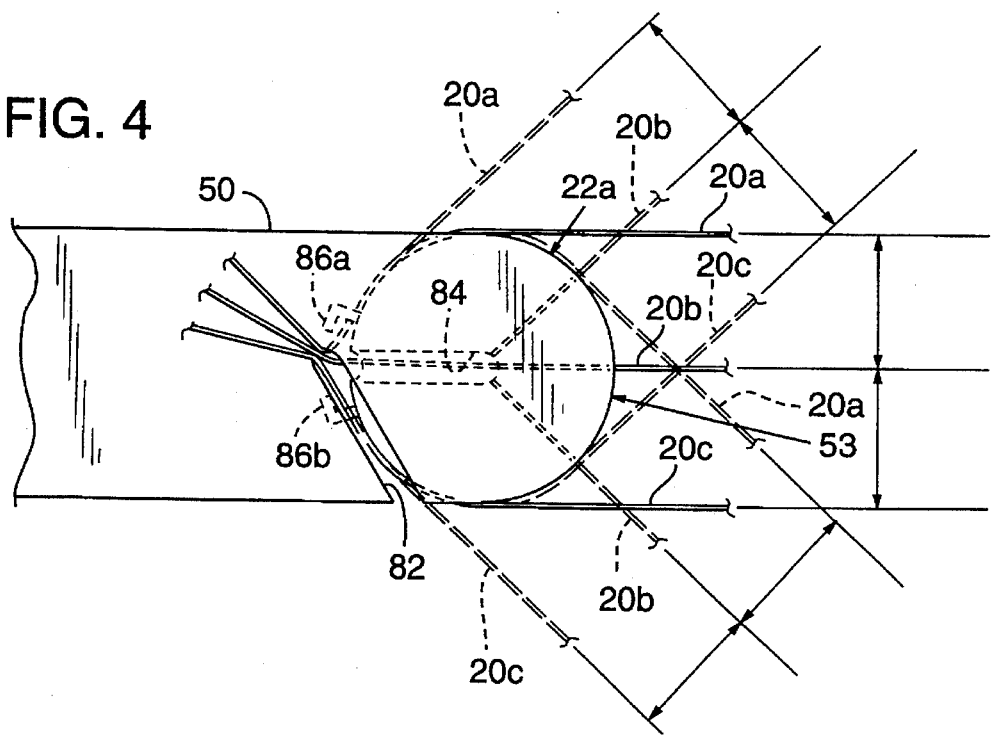
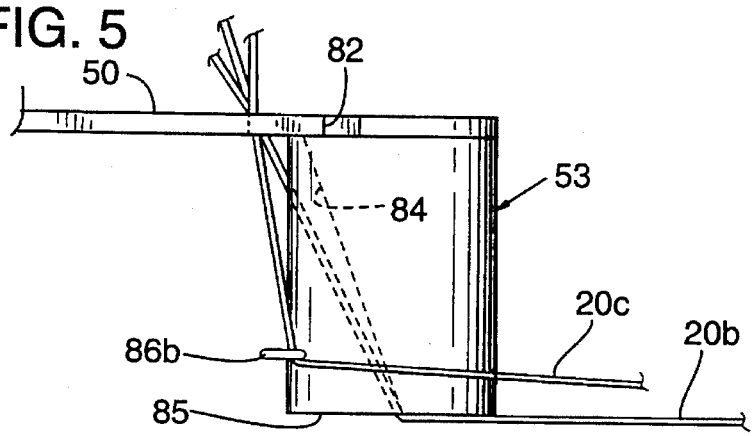

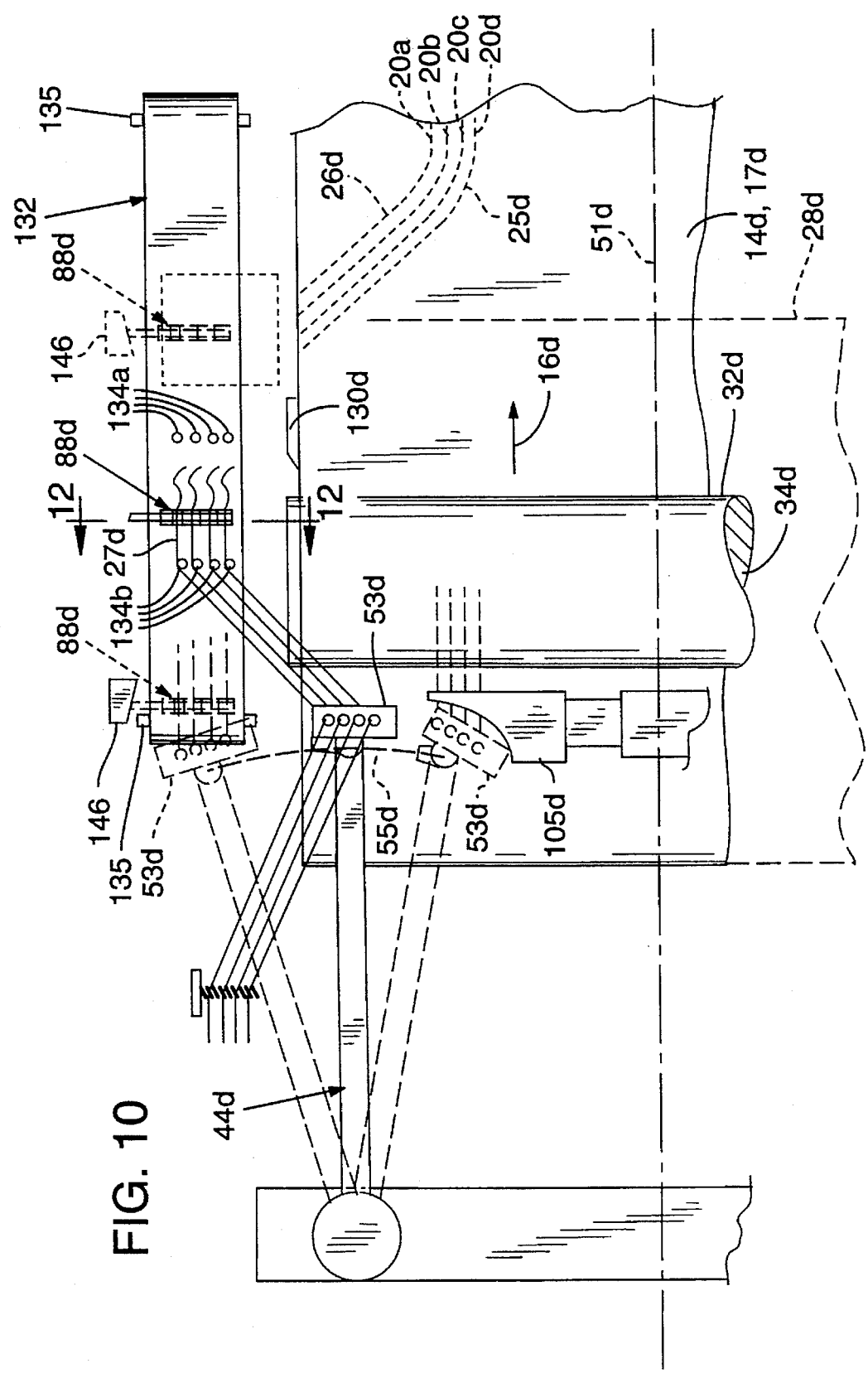

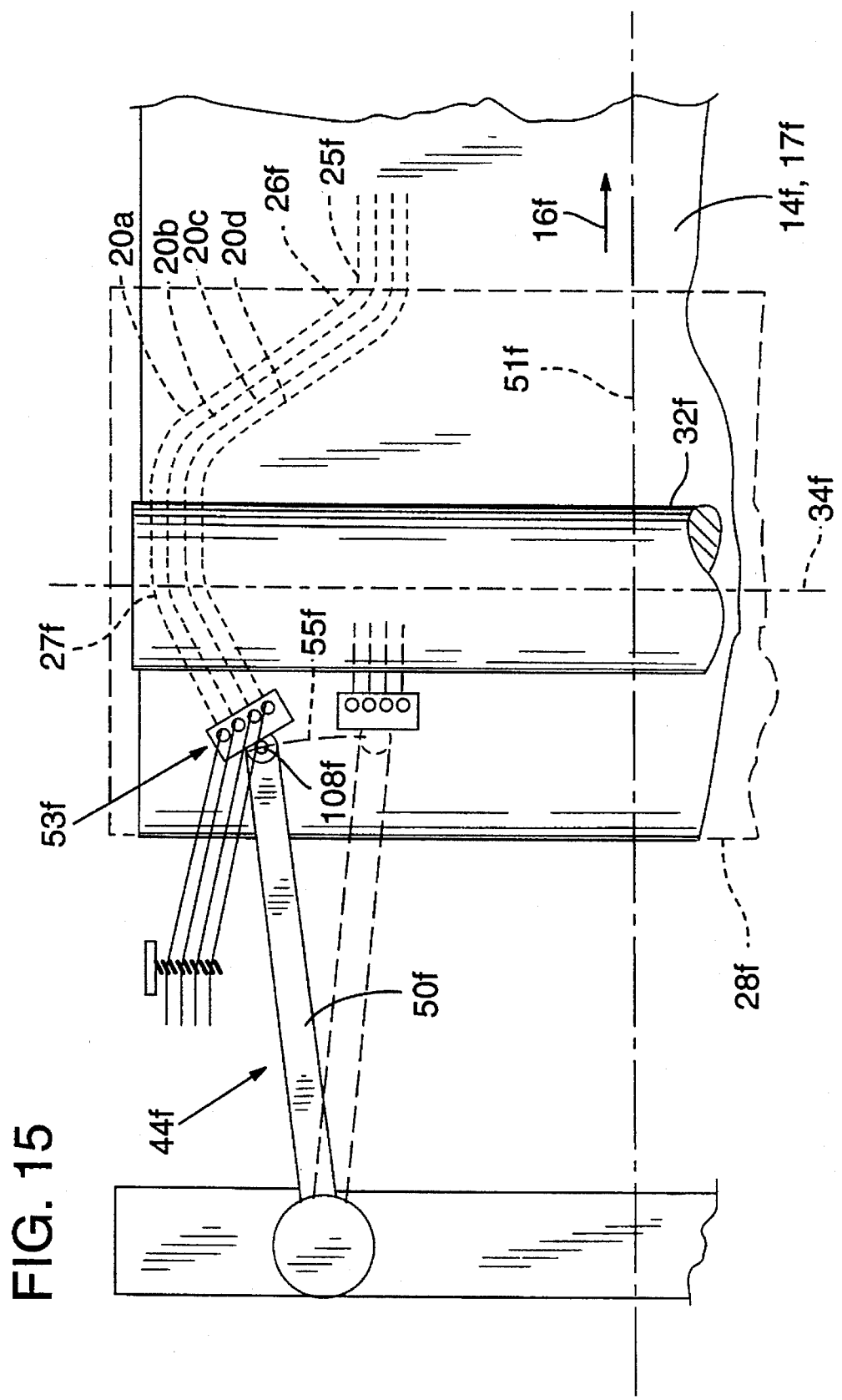

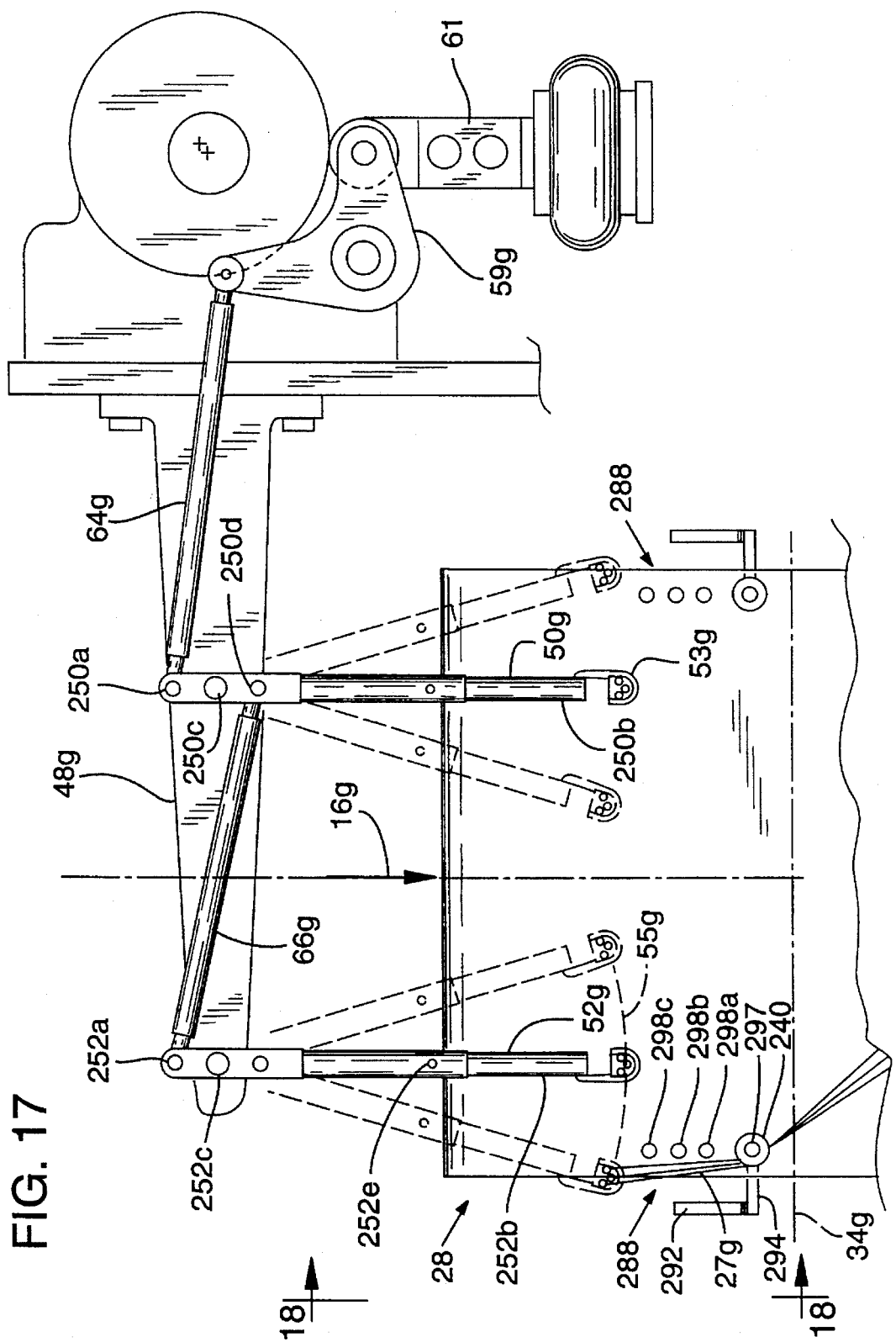

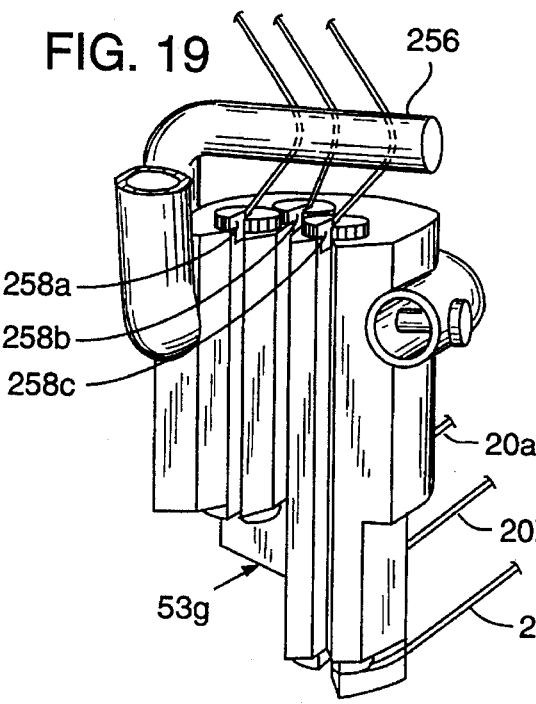
FIG. 19
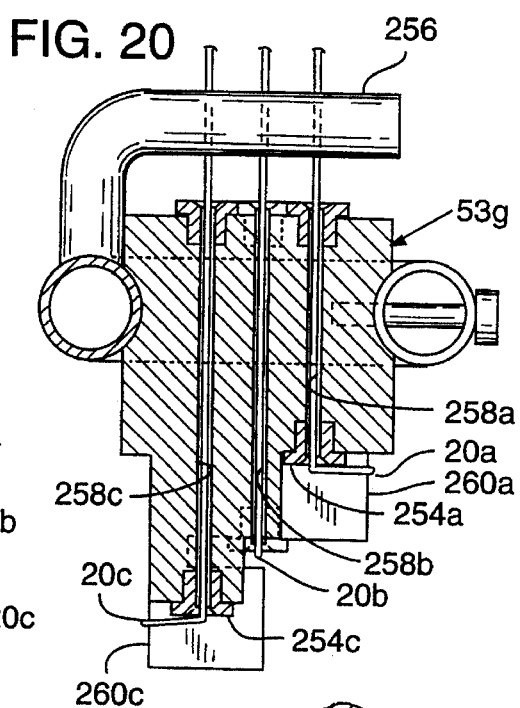
FIG. 20
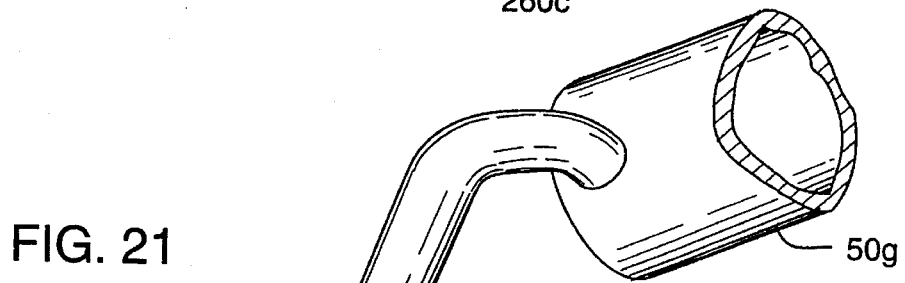
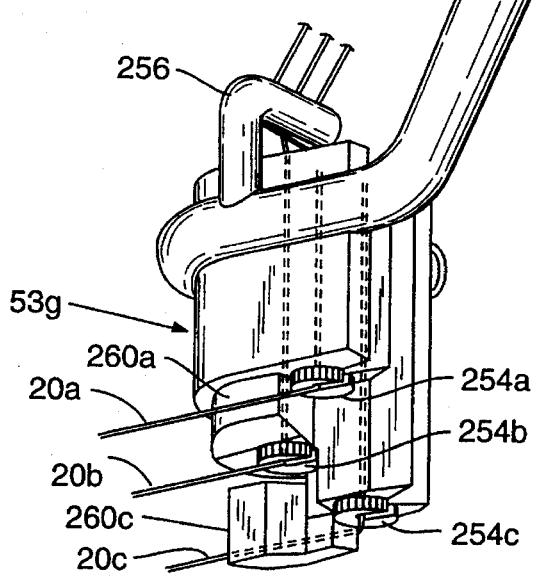
FIG. 21
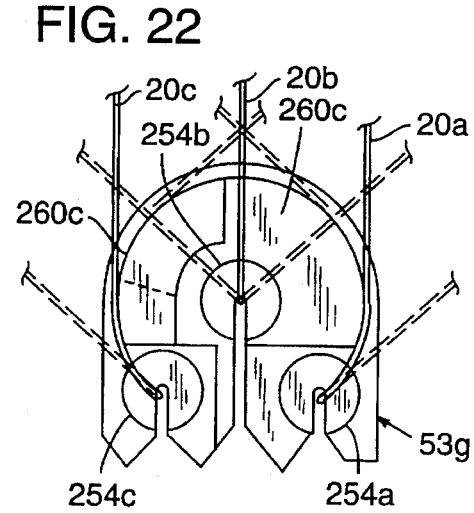
FIG. 22

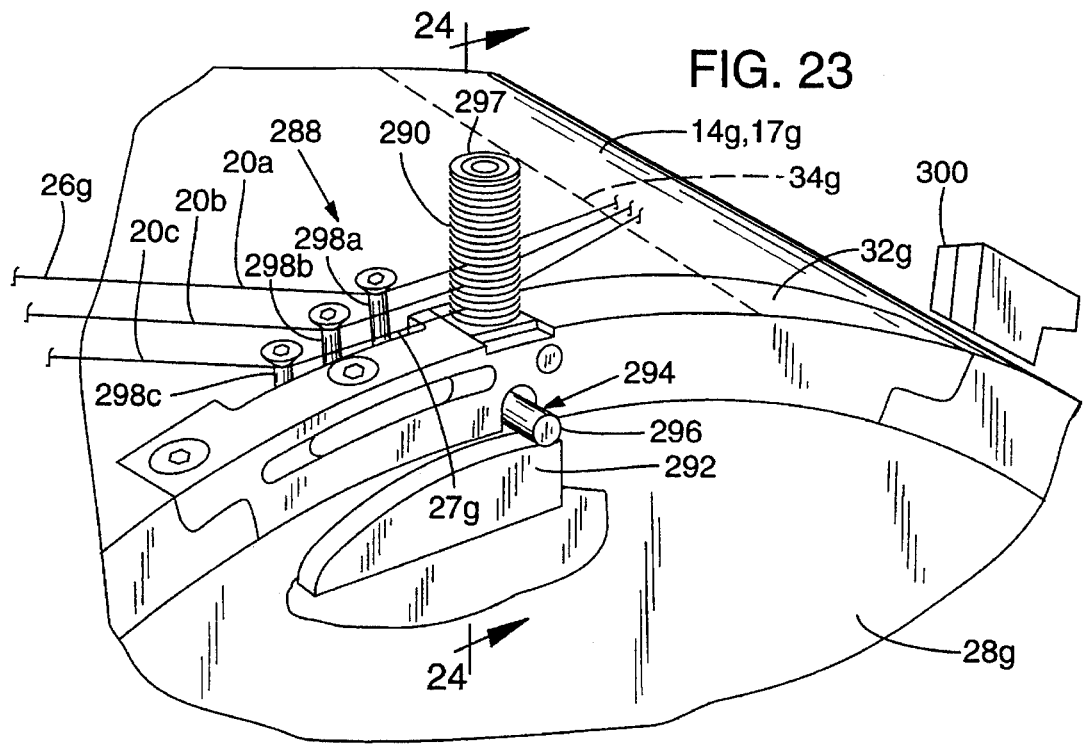
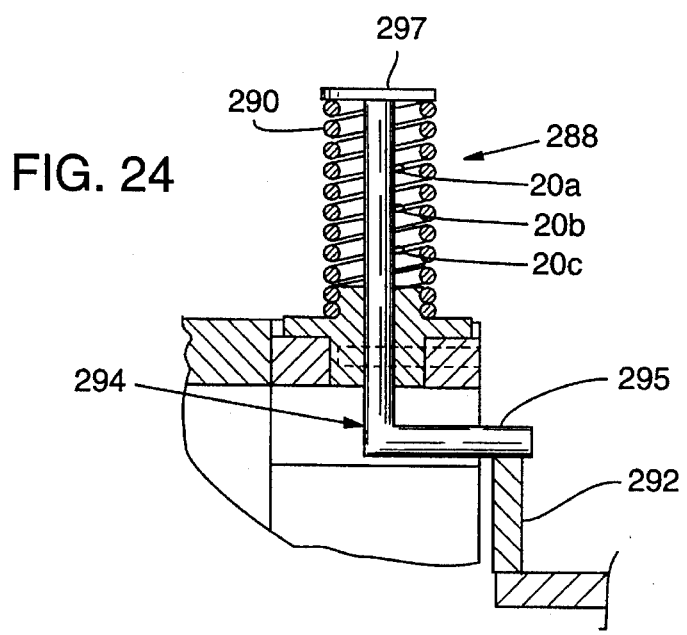

5,500,075

LEG ELASTIC APPLICATOR WHICH MAINTAINS THE SPACING BETWEEN THE ELASTICS SUBSTANTIALLY CONSTANT

FIELD OF THE INVENTION

The present invention is directed to apparatus and method for applying elastic to material, such as leg elastic on material for disposable diapers, training pants, and the like.

BACKGROUND AND SUMMARY OF THE INVENTION

Disposable absorbent garments, such as children's diapers and training pants, commonly incorporate elastic adjacent the leg openings of the garment for a snug fit that minimizes leakage from the garment leg region. The application of elastic along the leg openings in such garments has been the subject of a great deal of activity in the past.

In particular, elastic positioned along the leg openings in a curved contour has been found desirable in minimizing leakage. However, existing machines have not proved entirely satisfactory in economically applying elastic in curved patterns to such garments.

An object of the present invention is to provide a machine that applies elastic in an improved, curved contour to garment material.

Another object of the present invention is to provide a machine suitable for application of elastic at high working speeds.

It is a further object of the present invention to provide apparatus that economically applies such elastic.

A further object of the present invention is to provide apparatus that applies individual bands of elastic with selected spacing between the bands throughout the curved contour.

In accordance with the present invention, a machine for applying elastic to garment material is provided that includes a conveyor for carrying garment material. The conveyor moves in one direction along a flow path. An elastic band storage with a plurality of elongate elastic bands is provided for application to the garment material. An elastic feeder has a feeder head that feeds the plurality of elastic bands directly onto the garment material carried by the conveyor while the feeder head moves laterally across the flow path. The lateral movement of the feeder head across the moving conveyor applies the elastic bands to the material in a curved contour. The feeder head is further operable to feed the elastic bands onto the material while maintaining a selected spacing between individual elastic bands throughout the curved contour.

Also in accordance with the present invention, a method is provided for applying elastic to garment material that includes the steps of moving the material in one direction along a flow path, providing a source of a plurality of elongate elastic bands, guiding the elastic bands directly onto the material in a pattern moving laterally across said material relative to said one direction such that the elastic bands are applied to the material in a curved contour, and maintaining a selected side-to-side spacing between individual elastic bands throughout the curved contour.

BRIEF DESCRIPTION OF THE DRAWINGS

FIG. 3 is an enlarged exploded perspective view of a feeder head shown in FIGS. 1 and 2.

FIG. 4 is a top plan view of the feeder head shown in FIG. 3.

FIG. 5 is a side view of the feeder head shown in FIG. 3.

FIG. 10 is a cut-away top plan view of a machine for applying leg elastic to garment material according to yet another alternate embodiment of the present invention, Showing a portion of the machine on one side of the longitudinal center line of the machine.

FIG. 15 is a cut-away top plan view of a machine for applying leg elastic to garment material according to an additional alternate embodiment of the present invention, showing a portion of the machine on one side of the longitudinal center line of the machine.

FIG. 17 is a partially cut-away top plan view of a machine for applying leg elastic to garment material according to another alternate embodiment of the present invention.

FIG. 19 is an enlarged perspective view of the top of the feeder head of the embodiment shown in FIG. 17.

FIG. 20 is an enlarged view taken along line 20—20 in FIG. 18.

FIG. 21 is an enlarged perspective view showing the bottom of the feeder head of the embodiment shown in FIG. 17.

FIG. 22 is an enlarged bottom view of the feeder head of the embodiment shown in FIG. 17.

FIG. 23 is an enlarged perspective view showing one gripper of FIG. 17.

FIG. 24 is an enlarged view of a portion of the gripper of FIG. 17, showing a cam extending a gripper spring.

DESCRIPTION OF PREFERRED EMBODIMENTS OF THE INVENTION

Figure 1:
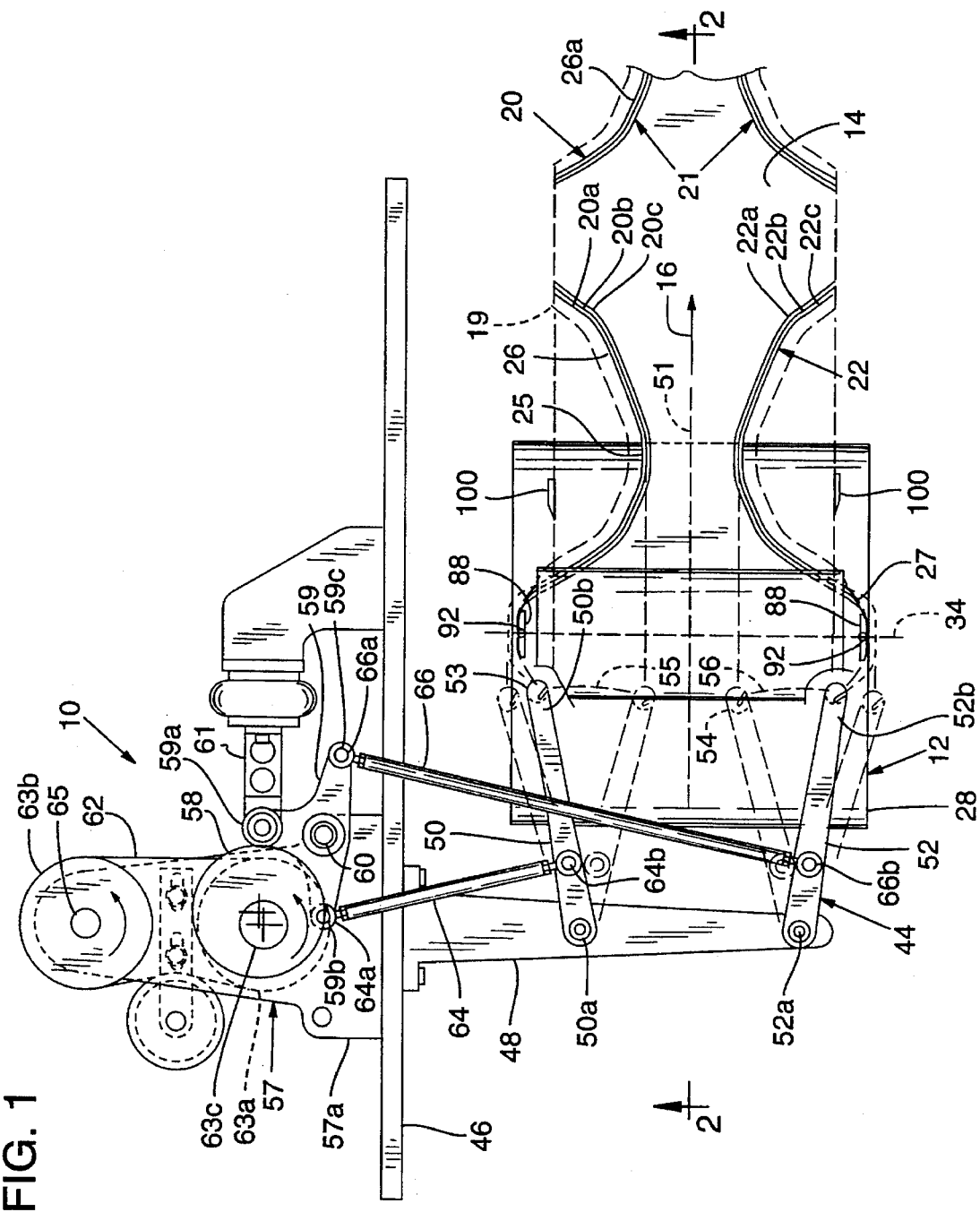
FIG. 1 is a top plan view of a machine for applying leg elastic to garment material according to an embodiment of the present invention, having portions broken away to reveal underlying structure.
Figure 2:
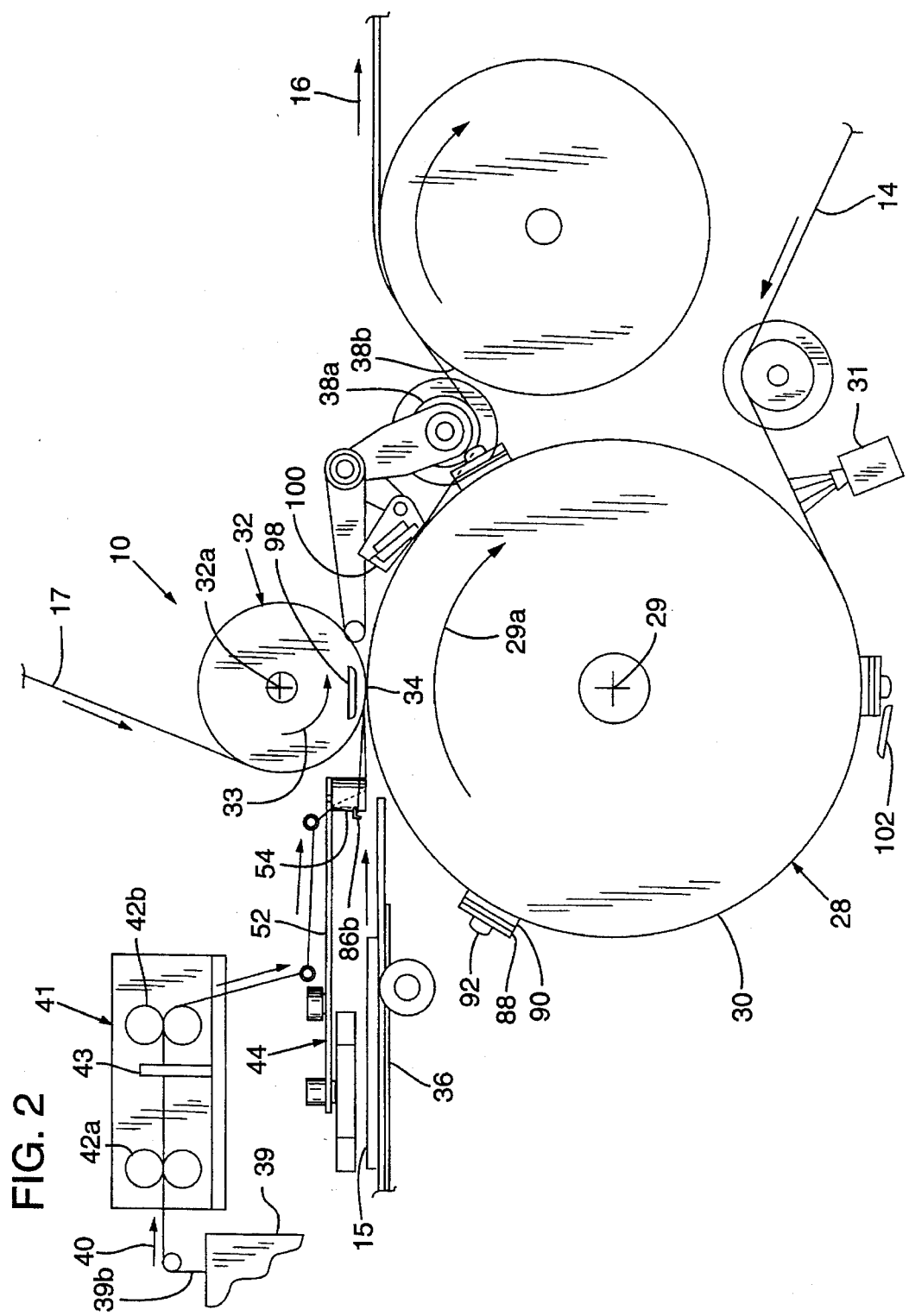
FIG. 2 is a side view of the embodiment of FIG. 1.

Referring first to FIGS. 1 and 2, apparatus generally indicated at 10 is constructed according to an embodiment of the invention. The apparatus illustrated is specifically adapted to produce disposable diapers or training pants, but it should be understood that it is not limited to such products.

As is known, disposable diapers and training pants generally include an outer, or backing, sheet of a liquid impervious material, onto which an absorbent pad is placed. A liquid pervious liner, or inner, sheet is placed thereon to encase the absorbent pad therebetween. One garment and method of manufacture is illustrated in U.S. Pat. No. 4,726,807 to Young and Lancaster, which is herein incorporated by reference to illustrate typical materials used and known methods of manufacturing such garments.

In the manufacture of such products it is often desirable to provide contoured strands, or bands, of elastic material extending generally longitudinally between the backing and liner sheets to produce elasticized leg opening areas for the garment produced. Since such products often are manufactured on assembly lines in which the garments material moves substantially continuously longitudinally, in what is referred to as the "machine direction," the elastic is placed on a moving web with the elastic stretched and extending generally longitudinally along the machine direction.

Referring to FIGS. 1 and 2, an elongate sheet, or web, of backing material 14 having a selected width is moved in one direction along a flow path 16 which extends in the machine direction. As is seen in FIG. 2, an elongate absorbent pad 15 is placed on backing material 14, and an elongate sheet of inner liner material 17 is laid thereover.

For example, the liquid impervious back sheet 14 may be of a thin thermoplastic material, such as a pigmented polyethylene film having a thickness in the range of 0.02–0.04 mm. The liquid pervious liner sheet 17 may be a carded polyester fiber with a latex binder or a spun-bonded polypropylene having continuous fibers and thermally bonded by patterned calendar rolls. The liner sheet may be impregnated with a surfactant to render it hydrophilic. The absorbent pad 15 may be of wood fibers or other fibers, such as chemical wood pulp, or any other suitable moisture absorbing material such as commercially available fluff pulp or a fluffed bleached craft soft wood pump.

A first and second set 20, 22 of elongate elastic elements, each set herein shown as including individual elastic bands 20a, 20b, 20c, and 22a, 22b, 22c, extending generally longitudinally along the flow path 16 and are adhered to the backing material 14. The first and second sets of bands 20, 22 are arranged in a symmetric, curved contour, or pattern 21 that generally resembles a repeating hour-glass pattern, with inboard regions 25, diagonal regions 26, and outboard regions 27. A contoured dashed line 19 positioned along the sets of bands 20, 22 indicate leg contour cut-out lines at which leg openings will be severed from the garment in the manufacturing process. The sets of bands 20, 22 will elasticize the leg opening regions of the garments produced.

Describing the apparatus, and referring still to FIGS. 1 and 2, a circular conveyer drum 28 is supported on and driven about a central axle 29. The direction of rotation is indicated generally by arrow 29a. The peripheral face 30 of the drum supports backing material 14 as it travels from the bottom side of the drum to the top side of the drum in FIG. 1. As is seen in FIG. 2, the drum is wider than the usual width of material to be carried thereon so that it can accommodate sheet material of different widths.

An adhesive applicator for applying adhesive to the side of the backing material sheet 14 that receives the elastic is generally indicated at 31. The adhesive applicator 31 preferably sprays adhesive onto the backing material upstream of the conveyor drum 28 to prevent accumulation of any possible overspray on the conveyor drum 28. The adhesive may be applied over the entire outward width of the backing material sheet 14 to provide adhesion for the sets of bands 20, 22 and pads 15.

A nip roller 32 is mounted above the conveyor drum 28 for powered rotation about an axle 32a substantially parallel to drum axle 29. The nip roller counter-rotates relative to the conveyor drum in the direction indicated by arrow 33 and presses against drum 28 at a nip 34. The roller 32 carries liner material 17 adjacent and overlying backing material 14. The sets of bands 20, 22 are pressed tightly between the drum 28 and the nip roller 32 at nip 34. This, as will be discussed later, serves to press the backing and liner materials 14, 17 tightly together over the sets of bands 20, 22.

A pad conveyor 36 is operable to carry longitudinally spaced pads 15 and insert them at the nip 34 into the space between backing sheet 14 and liner sheet 17, such that a pad will be carried by the backing and liner sheets through the nip between drum and roller 28, 32 and be captured between the two sheets.

The combined backing and liner sheet with an absorbent pad encased therebetween are carried downstream, to the right in FIGS. 1 and 2, and are supported on subsequent rollers 38a, 38b (FIG. 2) and other conveyor mechanism in the system as they are moved therealong.

Referring now more specifically to the apparatus for applying the sets of elastic bands 20, 22 and referring to FIG. 2, an elastic storage container is generally indicated at 39. An elongate strip of elastic material 39b is drawn from container 39 and carried in the direction of arrow 40. The elastic strip material already has been scored during its manufacture such that it is easily split into two sets 20, 22 of three elastic bands each 20a, 20b, 20c, and 22a, 22b, 22c.

An example of the elastic used is 0.015 inch by 0.027 inch, three-end natural rubber obtained from Fulflex. However, the elastic may be any form of elasticized material which may be found to be desirable for producing the product at hand. Examples of other materials which might be used are polyurethane, ribbon elastic, lycra strands, or others used in the industry.

A splitter device which produces this function and also provides initial tensioning of the strands is indicated generally at 41. This splitter device includes a first pair of powered counter-rotating rollers 42a between which the elastic strip 20 is moved. A second set of powered counter-rotating rollers 42b are positioned downstream from rollers 42a with the elastic bands moving between the rollers 42b. Rollers 42b are driven at a speed slightly higher than rollers 42a, such that the elastic band are stretched in tension. A plurality of spaced pins 43 are disposed between rollers 42a, 42b with the elastic bands being routed about the pins to separate the elastic strip 20 into six individual bands.

As shown in FIG. 1, an elastic feeder is positioned above the conveyor drum 28 and generally indicated at 44. An elongate support member 48 extends from a frame 46 laterally across a machine centerline 51 that extends along the center of the drum face 30 at the center of flow path 16. Elongate first and second swing arms 50, 52 are pivotally mounted to the support member 48 at proximal swing arm ends 50a, 52a. The swing arms 50, 52 are mounted symmetrically on either side of the machine centerline 51. The swing arms 50, 52 extend generally in the flow path direction and support elastic feeder heads 53, 54 at the distal swing arm ends 50b, 52b.

Arms 50, 52 are mounted to swing in a reciprocating, simultaneous and symmetric fashion across the flow path 16.

Accordingly, the feeder heads 53, 54 are swept in reciprocating, simultaneous and symmetric arcuate, mirror-image sweep paths 55, 56 that extend laterally across the flow path 16. Applying the sets of elastic bands 20, 22 from the reciprocating feeder heads directly to the moving sheet of backing material 14 produces the symmetric curved elastic "hour glass" contour 21.

Although the sets of bands 20, 22, shown in FIG. 1 are covered with liner material 17, they are shown in solid lines for clarity. The relatively small diameter of the nip roller 32 permits the feeder heads 53, 54 to be positioned close to the nip 34 to promote the precise application of the elastic bands.

As will be appreciated by attention to FIG. 1, the shape of the elastic contour 21 is related to the ratio of the rate of lateral motion of the feeder head across the flow path 16 (feeder rate) and the rate of motion of the conveyor drum face 30 in the flow path direction 16 (conveyor rate). In general, the elastic is applied at a maximum angle relative to the flow path 16 when the feeder rate is at its maximum speed. Accordingly, the maximum feeder rate corresponds to the contour diagonal portion 26. Conversely, the elastic is applied parallel with the flow path when the feeder rate is zero, meaning the feeder head 53 is stationary. Mathematically expressed, the elastic bands of the diagonal region 26 extend relative to the flow path 16 at an angle=arctan (feeder rate÷conveyor rate).

Arms 50, 52 are swung by a cam mechanism 57. The mechanism includes a cam mounting plate 57a that is mounted on the frame 46 and supports a horizontally rotating cam 58. The cam 58 actuates a rocker plate 59, which has a top corner 59a and opposing base corners 59b, 59c that generally describe the corners of a triangle. The plate 59 rocks about a vertical rocker post 60 received through the middle of the triangle base region. A roller at the plate top corner 59a is engaged by the cam 58 to rock the plate 59. A resilient biasing member 61 extending from the frame 46 engages the top corner 59a of the plate 59 to urge the roller into snug engagement with the cam 58. The snug engagement yields a smooth rocking action for the plate 59.

The shape of the curved elastic contour 21 is varied by varying the shape of the cam 58. In the preferred embodiment, the cam is shaped in a 6th order polynomial curve to obtain the complex curved contour 21 shown in FIG. 1. The preferred elastic contour 21 yields garments with leg elastic having varying selected curvature from front to rear about the garment leg openings. Thus, any of a variety of elastic curves that are effective in retaining moisture may be produced through application of the cam mechanism. If a simple smooth curved contour is desired, an eccentrically mounted circular cam could be used.

The cam mechanism 57 may be driven by a belt 62 and pulley 63a, 63b mechanism. A cam pulley 63a is mounted on cam shaft 63c beneath the cam 58 in planar registration with a drive pulley 63b that is mounted on a powered drive shaft 65. The belt 62 is trained about the pulleys 63a, 63b to drive the cam 58.

First and second connecting rods 64, 66 extend from proximal pivot attachments 64a, 66a at the opposing base corners 59b, 59c of the rocker plate 59, to distal pivot attachments 64b, 66b on intermediate portions of the swing arms 50, 52. The first connecting rod 64 is shorter than the second connecting rod 66. The rocker post 60 is positioned slightly downstream along the flow path 16 relative to the distal pivot attachments 64b, 66b, such that the connecting rods 64, 66 swing their respective swing arms 50, 52 through substantially identical swing angles. In this way, the attached feeder heads 53, 54 move through substantially identical arcuate paths 55, 56.

The feeder head 53 of FIGS. 1 and 2 is shown enlarged in FIGS. 3–5. The feeder head 53 is adapted to apply three elastic bands 20a, 20b, 20c with a constant, equi-distant spacing between adjacent elastic bands, throughout the curved elastic contour 21. Further details and alternative embodiments of the feeder will be discussed hereafter.

Preferred Embodiment

As shown in FIG. 1, the feeder heads 53, 54 extend downward from the distal ends of swing arms 50, 52. The feeder heads are cylindrical and oriented generally perpendicular to the flow path 16. The feeder heads 53, 54 are fixed relative to the swing arms 50, 52.

As shown enlarged in FIGS. 3–5, a diagonal slot 82 in the swing arm 50 guides the elastic bands 20a, 20b, 20c to the feeder head 53. The slot 82 is cut into the inboard portion of the swing arm 50 adjacent the feeder head 53 and extends rearward (opposite the flow path 16) to the longitudinal center of the swing arm 50.

The three bands 20a, 20b, 20c are guided from above through the diagonal slot 82 to the feeder head. A central band 20b is guided through a central slot 84 in the feeder head 53. The central slot 84 extends diagonally from the top edge of the feeder head to the center of the bottom surface 85 of the feeder head 53. The top of the central slot 84 is positioned adjacent the terminus of the diagonal slot 82 at the swing arm centerline. The central band 20b extends through the central slot 84 for constant application from the center of the feeder head bottom.

The outermost elastic bands 20a, 20c are guided through a pair of opposing, L-shaped guides 86a, 86b around the circular periphery of the feeder head 53. The L-shaped guides 86a, 86b extend horizontally from a rear portion of the cylindrical feeder head 53. Each L-shaped guide 86a, 86b has a distal leg directed inwardly toward the opposite L-shaped guide. The guides 86a, 86b are closely spaced such that the outer elastic bands 20a, 20c are constantly applied tangentially from the cylindrical feeder head 53. The feeder head has a diameter equal to the selected spacing between the outermost individual elastic bands 20a, 20c.

The constant application of the central elastic band 20b from the center of the cylindrical feeder head 53, and the constant application of the outermost elastic bands 20a, 20c tangentially from the periphery of the feeder head 53, yield a constant equi-distant spacing between adjacent bands 20a, 20b, 20c throughout the curved elastic contour 21. FIG. 1 shows an overview of such an elastic contour 21.

The cylindrical feeder head 53 may also be utilized to apply a single elastic band through the central slot, or about the head periphery. Alternatively, the feeder head 53 may apply a pair of elastic bands with constant equidistant spacing. In this case one of the bands may be guided through the central slot 84 and one about the head periphery, or both bands may be guided about the head periphery.

In another aspect of the invention, elastic grippers 88 are fixed at intervals along the opposing outboard edges of the conveyer drum face 32, as shown in FIG. 1. The width of the material sheets 14, 17 is selected such that the material is positioned between the grippers 88. The nip roller 32 is longitudinally somewhat shorter than the drum conveyer 28, so that the nip roller 32 rotates between the opposing grippers 88.

The grippers are adapted to hold the elastic bands 20a, 20b, 20c of the outboard contour region 27 in tension outboard of the material. As shown in FIG. 1, the feeder head 53 sweeps laterally to an outboard position adjacent the grippers 88 such that the elastic bands 20 are applied outboard of the material 14, 17, nip roller 32, and gripper 88. The elastic bands 20 applied outboard of the grippers 88 and nip roller 32 are not pinched at the nip 34 and thus contract inward into engagement with the gripper 88.

Figure 6:
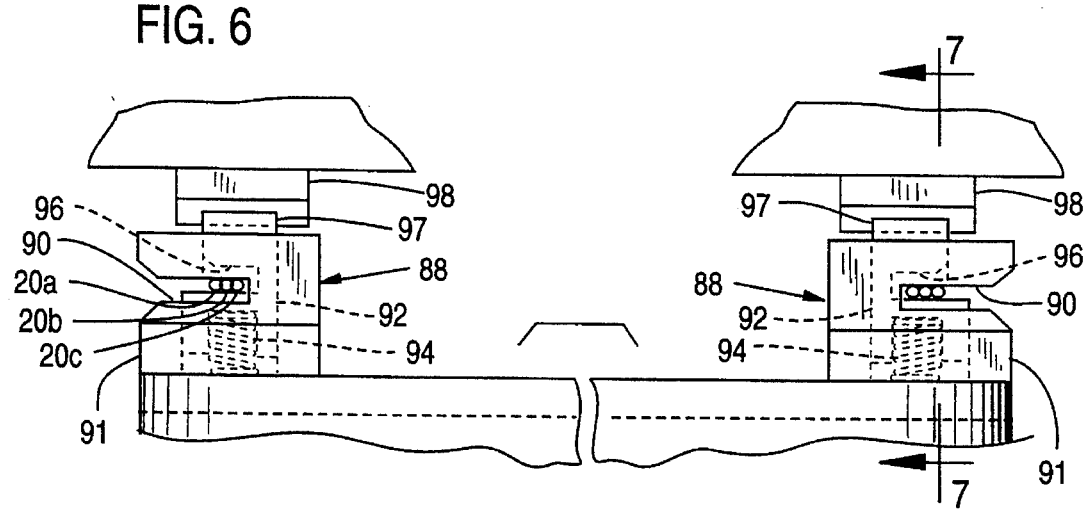
FIG. 6 is an enlarged end view of elastic grippers shown in FIGS. 1 and 2, with the drum conveyor on which the grippers are mounted shown cut-away.
Figure 7:
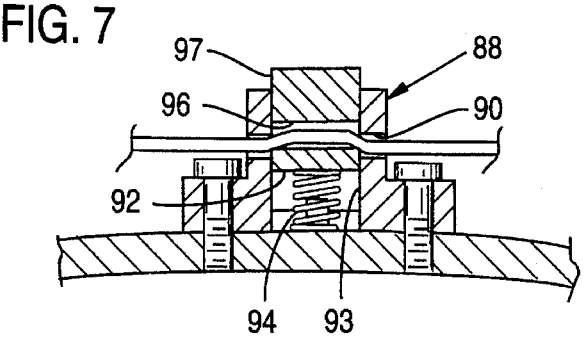
FIG. 7 is an side view of one elastic gripper shown in FIG. 6.

As shown enlarged in FIGS. 6 and 7, the gripper 88 is elongate and has a longitudinal slot 90, or holding bay, in the outboard face 91 that receives the contracting elastic bands 20. A locking pin 92 having a notch 96 extends through a bore 93 in the gripper and is actuable to grip the elastic bands 20 within the slot 90. The pin 92 is mounted upon a coil spring 94 to normally bias the pin upwardly to a lock position. In the lock position, the pin notch 96 moves into an upper portion of the bore 93, and the top 97 of the pin 92 protrudes from the top of the gripper 88.

To receive the elastic bands 20a, 20b, 20c, a stationary cam 98 depresses the locking pin top 97 such that the pin notch 96 moves downwardly into alignment with the slot 90. As shown in FIG. 2, the cam 98 is fixed adjacent the nip 34 to depress the locking pin 92 as the elastic is applied outboard of the gripper 88. The cam 98 releases the pin 92 downstream of the nip 34 to return the pin 92 to the lock position wherein the elastic is gripped between the bottom of the notch 96 and the top of the longitudinal slot 90.

The elastic bands 20a, 20b, 20c gripped by the grippers 88 extend outwardly in tension from opposing edges of the overlaid sheets 14, 17 of garment material. A cutting blade 100 mounted downstream of the nip 34 severs the gripped outboard elastic bands adjacent the edges of the overlaid sheets 14, 17.

The grippers 88 release the severed lengths of elastic adjacent the bottom side of the drum 28. stationary release cams 102 are positioned on either side of the bottom of the conveyor drum 28 to depress the locking pins 92 and permit the severed lengths of elastic to fall out of the grippers 88.

Since the outboard elastic contour region 27 is scrapped in this embodiment, a garment is formed with elastic bands 20a, 20b, 20c extending about the leg openings, but not fully up the sides of the garment.

Alternate Embodiment No. 1

Figure 8:
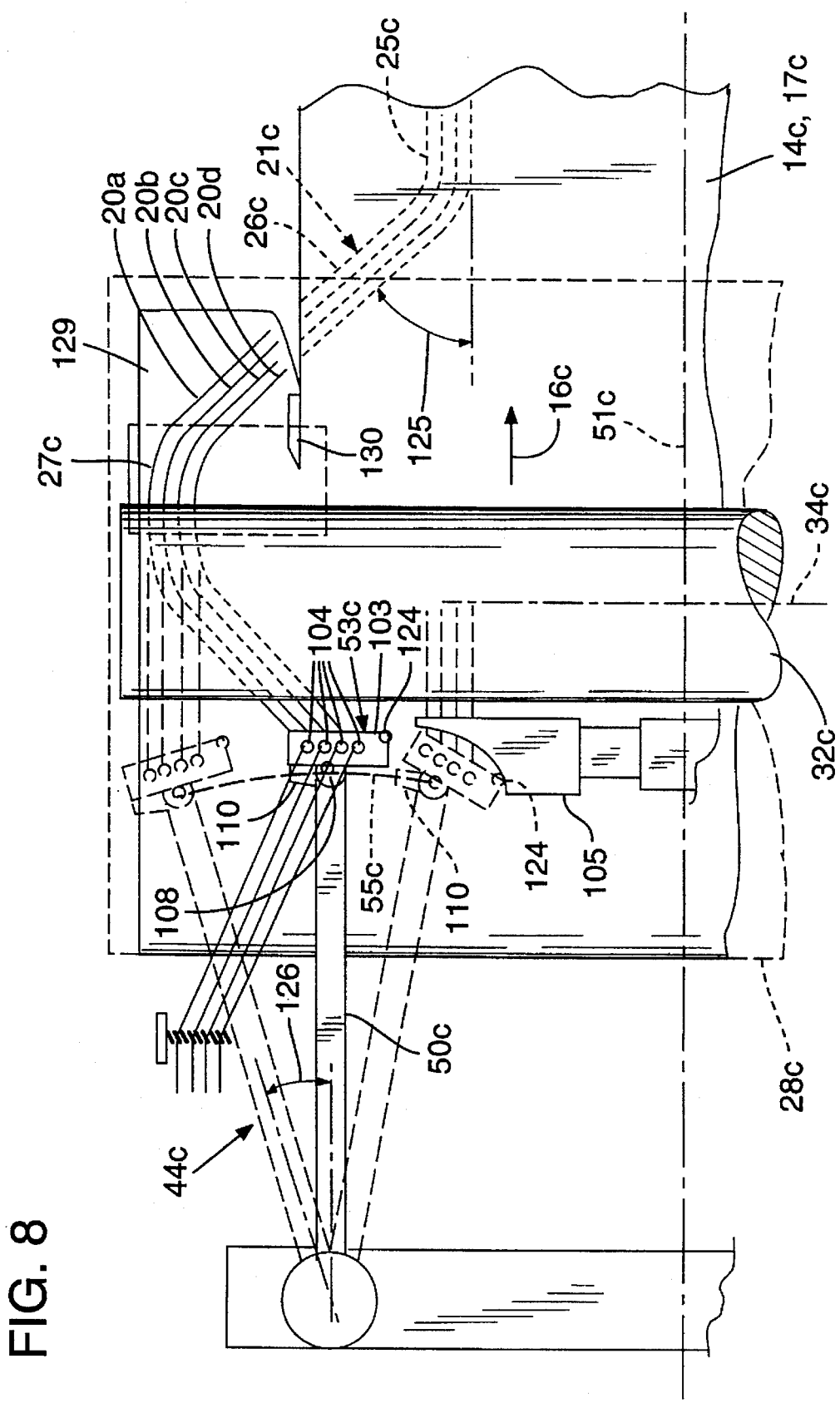
FIG. 8 is a cut-away top plan view of a machine for applying leg elastic to garment material according to an alternate embodiment of the present invention, showing a portion of the machine on one side of the longitudinal center line of the machine.

FIGS. 8 shows a machine embodiment with a pivotal feeder head 53c that permits selected spacing between a plurality of individual elastic bands. In this case, the feeder head is adapted to apply four bands 20a, 20b, 20c, 20d.

Figure 9:
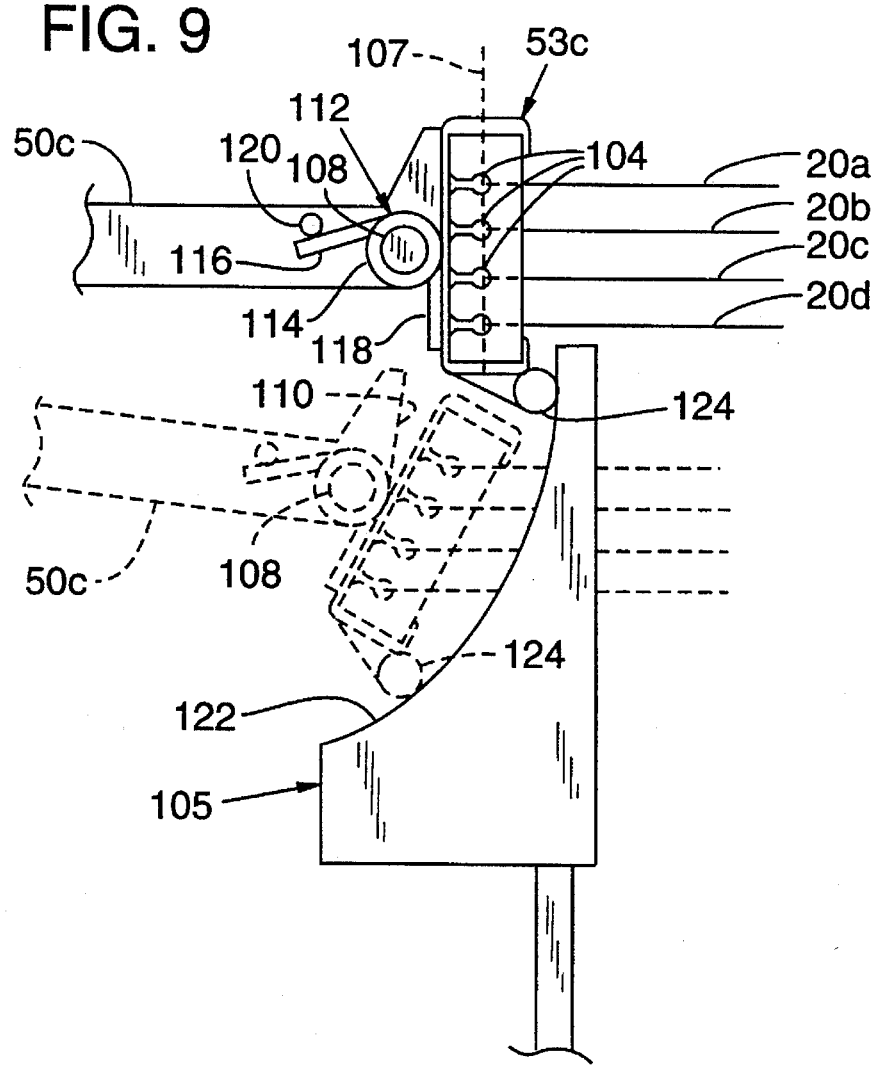
FIG. 9 is an enlarged top view of the feeder head of the embodiment shown in FIG. 8.

As best shown in FIG. 9, the feeder head 53c is pivotally attached to the distal end of the swing arm 50c. The feeder head 53c is block-shaped, with four elastic outlet apertures 104 for applying the four elastic bands. The apertures 104 extend vertically through the head in a fixed spatial relation to one another, and are aligned in an aperture line 107 extending across the bottom surface of the head 53c. The elastic bands 20a–20d are guided through the top of the apertures 104 and exit the bottom of the apertures along the aperture line 107.

The feeder head 53c pivots about a vertical pivot pin 108 at the distal end of the swing arm 50c. The distal end of the swing arm 50c has an enlarged orientation surface 110 extending perpendicular to the length of the swing arm 50c. A biasing means, such as a torsion spring 112, biases the feeder head 53c against the orientation surface 110 to normally orient the aperture line 107 substantially perpendicular to the length of the swing arm 50c.

The torsion spring 112 has a coiled portion 114 that is centered about the pivot pin 108. First and second lever arms 116, 118 extend from opposite ends of the coil 114. The first lever arm 116 is held static by an anchor pin 120 extending from the top of the swing arm 50c. The second lever arm 118 engages the feeder head 53c to pivotally bias it against the orientation surface 110.

A cam 105 is positioned adjacent the inboard portion of the arcuate path 55c (FIG. 8) traced out by feeder head 53c to selectively pivot the feeder head. The cam 105 has a curved cam face 122 that is engaged by a roller 124 on the inboard downstream corner of the feeder head 53c. The elastic bands 20a–20d extend from the aperture line 107 beneath the cam 105 for application adjacent the nip 34c.

As best appreciated by referring to FIG. 8, the selected pivoting of feeder head 53c, and thus the contour of the cam face 122, is related to the foregoing discussion of the ratio of the feeder rate and conveyor rate. With this relationship in mind, the application of the elastic contour regions 25c, 26c, 27c will now be described.

The diagonal elastic portion 26c is applied when the swing arm 50c is substantially parallel to the flow path 16c. In other words, the aperture line 107 is substantially perpendicular to the flow path 16c. Since the bands 20a, 20b, 20c, 20d extend diagonally from the aperture line 107, the spacing between the elastic bands of the diagonal portion 26c is narrower than the spacing between the apertures 104. The spacing becomes narrower as the angle (designated by arrow 125) between the contour diagonal portion 26c and the flow axis 16c increases. Expressed mathematically, the spacing between the individual elastic bands 20a–20d= (spacing between outlet apertures 104)×cos (angle 125).

The feeder rate momentarily becomes zero at each end of the arcuate path 55c. At the outboard end of the arcuate path 55c where the outboard elastic region 27c is applied, the swing arm 50c is slightly angled from the flow path 16c by one-half of the included angle (designated by arrow 126) of the arcuate path 55c. Thus, the aperture line 107 is angled from the perpendicular to the flow path 16c by the same amount. The elastic is applied parallel to the flow path 16c so that the spacing between the individual elastic bands 20a–20d is slightly less than the spacing between the apertures 104 (but greater than the spacing between the bands of the diagonal portion 26c). Mathematically described, the spacing between the elastic bands of the outboard region 27c=(spacing between the outlet apertures 104)×cos (angle 126).

At the inboard end of the arcuate path 55c where the inboard elastic region 25c is applied, the cam 105 pivots the feeder head 53c to avoid the relatively wide spacing of the outboard region 27c. The cam 105 pivots the feeder head 53c so that the elastic bands exit from the outlet line 107 at an angle generally equal to the angle of the diagonal region 26c relative to the flow axis 16c. Therefore, the spacing between the elastic bands 20 of the inboard region 25c and diagonal region 26c is substantially equal.

In order to maintain the equal spacing, the cam 105 gradually pivots the feeder head 53c as the feeder rate decreases near the inboard end of the arcuate path 55c. Expressed mathematically, the aperture line 107 pivots by an angle=arctan ((maximum feed rate−feed rate)÷(conveyor rate)). Thus, at the inboard end of the arcuate path 55c where the feed rate is equal to zero, the aperture line 107 is pivoted at an angle= arctan (maximum feed rate÷conveyor rate).

In another aspect of this embodiment, the entire elastic contour 21c is encased between the overlaid backing sheet 14c and liner sheets 17c. To encase the entire elastic contour, the drum 28c and nip roller 32c are as least as long as the width of the material 14, 17. No grippers are required.

An outboard margin portion 129 of the backing and liner sheets, including the encased outboard elastic region 27c, is trimmed away as waste. A cutting blade 130 is fixedly positioned for this purpose downstream of the nip roller 32c. Thus, a garment is formed with elastic bands 20a–20d extending about the leg openings, but not completely up the garment sides.

Alternate Embodiment No. 2

Figure 11:
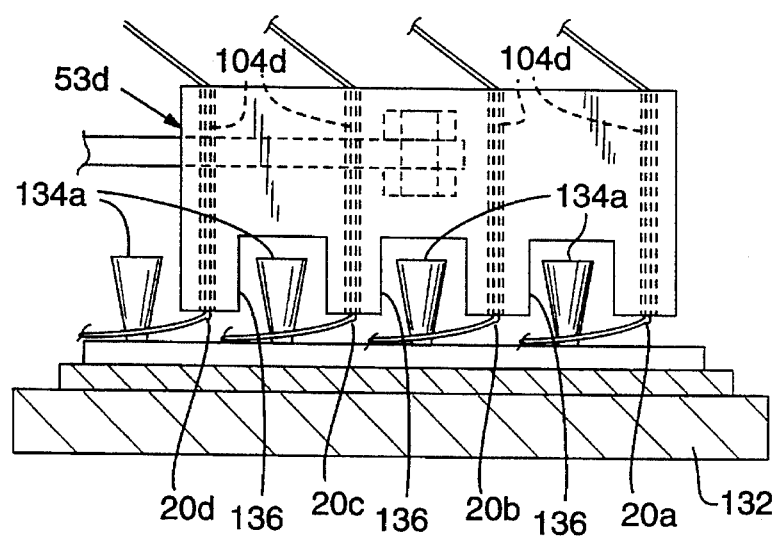
FIG. 11 is an enlarged elevational view of the feeder head and leading positioning fingers of FIG. 10.
Figure 12:
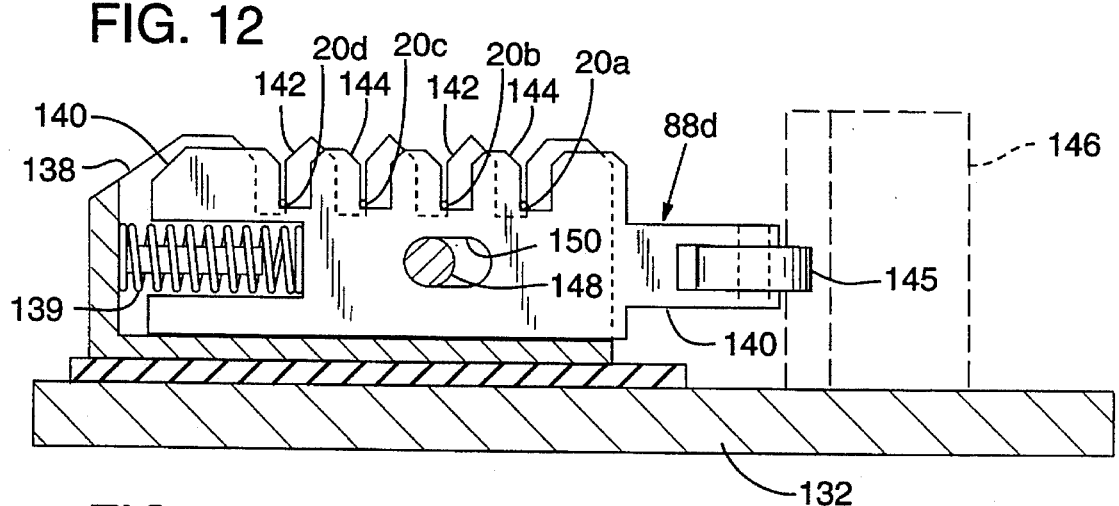
FIG. 12 is an enlarged view taken along line 12—12 in FIG. 10.

FIGS. 10–12 show another alternative embodiment with a cam 105d and pivotable feeder head 53d similar to those shown in FIGS. 8 and 9. The feeder head 53d is pivoted by a cam 105d at the inboard end of the arcuate path 55d to maintain constant spacing between elastic bands at the inboard 25d and diagonal 26d contour portions.

As shown in FIG. 10, however, the outboard contour regions 27d extend laterally outboard of the edge of the material sheets 14d, 17d. The outboard extending elastic regions 27d are gripped in tension by elastic grippers 88d. The grippers 88d are mounted at intervals on a second conveyor 132 to receive the bands of each outboard elastic region 27d. The second conveyor 132 runs parallel to one side of the flow path 16d at a speed equal to the conveyor speed. The conveyor 132 may run about a pair of powered spaced rollers 135.

The feeder head 53d moves adjacent the gripper 88d when at the outboard end of the arcuate path 55d. When so positioned, the feeder head 53d applies the bands 20a, 20b, 20c, 20d to the gripper 88d.

The gripper first receives the bands between a plurality of vertical positioning fingers 134a that extend in a row transversely across the second conveyor 132. As shown in FIG. 11, the bottom surface of the feeder head 53d has a plurality of protruding feeder fingers 136 through which the outlet apertures 104d extend. The moving positioning fingers 134a interdigitate with the feeder fingers 136 such that the elastic bands 20a, 20b, 20c, 20d are fed between the positioning fingers 134a.

The tension in the elastic bands 20 causes the bands to move into position against the positioning fingers 134a. The fingers have substantially inverted conical shapes that securely urge the elastic bands 20a, 20b, 20c, 20d downwardly toward the second conveyor 132.

Figure 13:
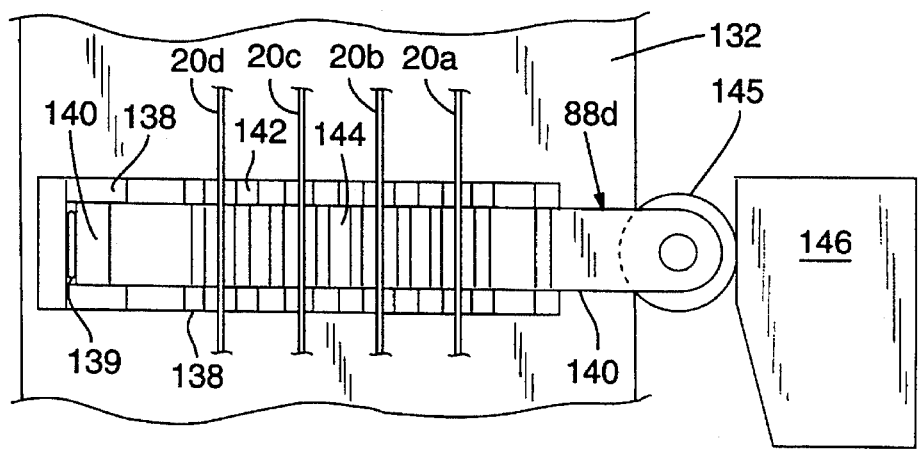
FIG. 13 is a top plan view of the elastic gripper and cam shown in FIG. 12.

As the second conveyor continues and the feeder head 53d remains at the outboard stationary position, the bands 20a, 20b, 20c, 20d are further threaded through the gripper 88d. As shown in FIGS. 12 and 13, the gripper 88d includes a pair of gripper plates 138 that sandwich a slidable spring-biased locking plate 140 therebetween. A pin 148 fixed in both gripper plates 138 extends through an elongate slot 150 in the locking plate to interconnect the plates 138, 140.

The gripper plates and locking plate, respectively, have a plurality of upwardly oriented gripper fingers 142, and locking fingers 144. The locking plate 140 is ordinarily biased by the spring 139 to offset the gripper and locking fingers 142, 144 in a lock position (FIG. 12).

The locking plate 140 has a roller 145 that is engagable by a stationary cam 146 to slide the locking plate to an open position. As shown in FIG. 13, the gripper and locking fingers 142, 144 are aligned to interdigitate with the feeder fingers 136 in the open position. In this fashion, the feed head positions the bands 20a, 20b, 20c, 20d between the open fingers 142, 144 of the gripper 88d.

As the gripper 88d moves past the feeder head 53d, the cam 146 releases the locking plate to return the gripper 88d to the lock position wherein the bands are gripped between the offset fingers 142, 144 (FIG. 12).

A trailing row of positioning fingers 134b, similar to fingers 134a, next interdigitate with the feeder fingers 136 to position the trailing bands of the outboard contour region 27d. The feeder head 53d then swings inboard to apply the diagonal elastic region 26d. As best illustrated in FIG. 10, the leading and trailing fingers 134a, 134b position the elastic bands such that the diagonal contour region 26d relative to the flow axis 16d is at a selected angle.

As shown in FIG. 10, the outboard elastic region 27d gripped by the gripper 88d is severed at the edge of the assembled material sheets 14d, 17d. A stationary cutting blade 130d is positioned downstream from the roller 32d to first sever the leading bands of the outboard contour 27d. The trailing bands of the outboard contour region 27d remain held in tension by the gripper 88d until severed by cutter 130d.

Alternate Embodiment No. 3

Figure 14:
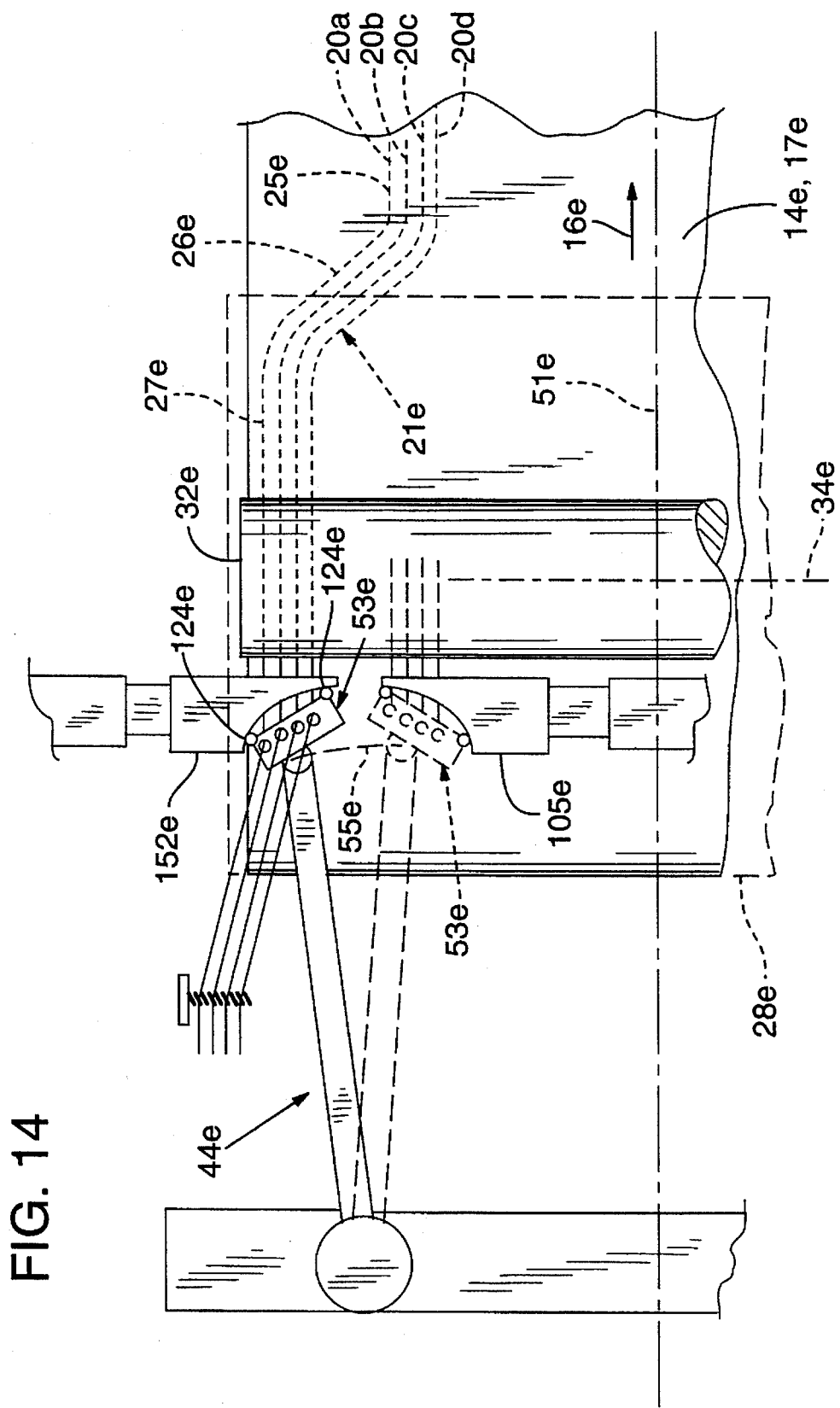
FIG. 14 is a cut-away top plan view of a machine for applying leg elastic to garment material according to another alternate embodiment of the present invention, showing a portion of the machine on one side of the longitudinal center line of the machine.

The embodiment shown in FIG. 14 has a pair of cams 105e, 152e positioned at both ends of the arcuate feeder head path 55e to provide constant spacing between the individual elastic bands 20 throughout the inboard, diagonal, and outboard elastic regions 25e, 26e, 27e.

Cam 105e is positioned adjacent the inboard end of arcuate path 55e to pivot the feeder head 53e as described in the first alternate embodiment (FIGS. 8 and 9). As shown in FIG. 14, opposing cam 152e is positioned adjacent the outboard end of arcuate path 55e to similarly pivot the feeder head 53e as the bands 20a, 20b, 20c, 20d of the outboard elastic region 27e are applied.

The feeder head 53e has rollers 124e at both ends for engaging the opposing cams 105e, 152e.

Feeder head 53e is somewhat similar to feeder head 53c of FIGS. 8 and 9. However, feeder head 53e must be able to pivot on both sides of the distal end of swing arm 50e. Thus, as shown in FIG. 14, the swing arm 50e does not have an enlarged distal orientation surface.

Feeder head 53e may be provided with resilient biasing means to normally urge the feeder head into a perpendicular position at the distal end of swing arm 50e. Alternatively, the opposing cams 105e, 152e may be extended to abut and form a unitary cam surface. Such a unitary cam may continuously position the feeder head if both rollers 124e continuously engage unitary cam surface, in which case no biasing means is needed.

The material sheets 14e, 17e have a selected width to encase the entire elastic contour 21e. Thus, there is no need for scrapping a margin portion of the material. In this way, a garment is produced with an elastic contour 21e having constant spacing between the bands 20a–20d, and extending completely up the sides of the garment.

Alternate Embodiment No. 4

Figure 16:
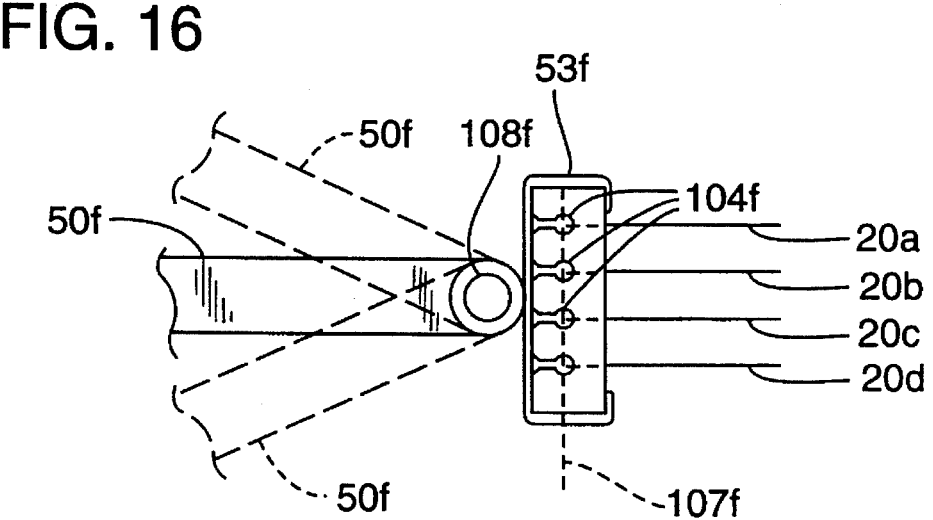
FIG. 16 is an enlarged top view of the feeder head of the embodiment shown in FIG. 15.

The embodiment shown in FIGS. 15 and 16 has a feeder head 53f that is freely pivotable about a vertical pivot shaft 108f at the distal end of the swing arm 50f.

The feeder head 53f is freely pivoted by the tension of the elastic bands 20a, 20b, 20c, 20d held at the nip 34f, as the feeder head 53f moves laterally across the flow path (FIG. 15). The pivoting is such that the elastic bands 20 generally always extend perpendicular to the aperture line 107f.

Thus, in a machine environment without grippers 88, 88d, the applied elastic bands 20a, 20b, 20c, 20d always have a spacing equal to the spacing between the outlet apertures 104f. In such an embodiment, band spacing remains constant throughout the inboard 25f, diagonal 26f, and outboard contour regions 27f. Mathematically expressed, the aperture line 107f is pivoted to an angle relative to the flow path 16f= arctan (feeder rate÷conveyor rate).

FIG. 15 shows materials 14f, 17f having a selected width to completely encase all regions 25f, 26f, 27f of the elastic contour. While no trimming of an material edge margin is shown, such trimming may be undertaken if desired.

Alternative Embodiment No. 5.

FIGS. 17–24 shows another embodiment of a leg elastic applicator. As shown in FIG. 17, swing arms 50g, 52g are pivotally reciprocated across the flow path 16g by first and second connecting rods 64g, 66g. First rod 64g interconnects the rocker plate 59g and the swing arm 50g, and second rod 66g interconnects the pair of swing arms 50g, 52g. Such a connecting configuration permits a relatively short second rod 66g to help minimize connecting arm inertia during machine operation.

Arm 50g pivots about a pivot shaft 250c extending from a support member 48g. The upstream end of arm 50g is pivotally attached to connecting rod 64g at a pivot shaft 250a, spaced a selected distance from pivot shaft 250c.

Connecting rod 66g is pivotally attached to arm 50g at a pivot shaft 250d, which is spaced an equal selected distance downstream from the shaft 250c. Rod 66g extends to attach at a pivot shaft 252a on the upstream end of swing arm 52g. Swing arm 52g pivots on the support member 48g at pivot shaft 252c, which is spaced the selected distance downstream from shaft 252a. The equal selected spacings between pivot shafts permit the swing arms 50g, 52g to pivot symmetrically through identical swing angles.

Figure 18:
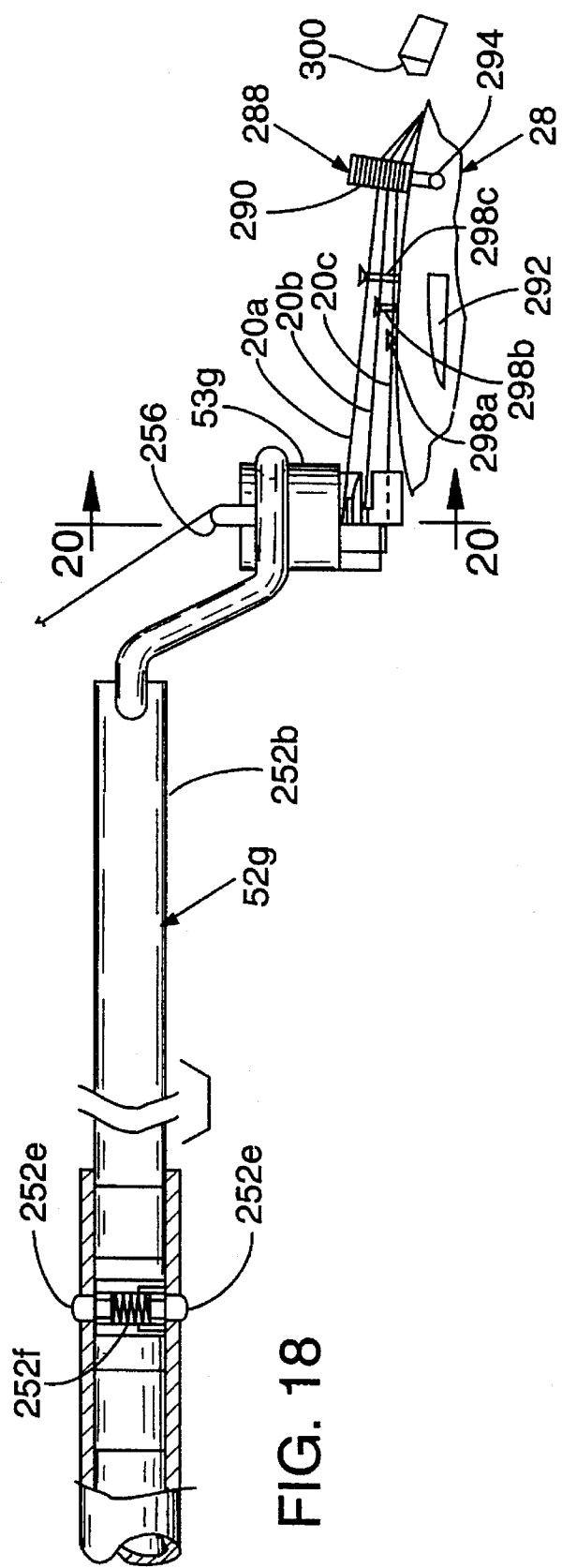
FIG. 18 is a view taken along line 18—18 in FIG. 17.

Swing arms 50g, 52g are telescopic. As best seen in FIG. 18, buttons 252e supported by spring 252f protrude from the top and bottom of swing arm 52g to lock the arm in an extended position. The buttons 252e may be manually depressed into the arm so that a distal portion 252b of the arm 52g may be telescopically retracted into the arm.

As shown in FIGS. 19–22, this embodiment has a feeder head 53g that applies three elastic bands 20a, 20b, 20c from three platforms 254a, 254b, 254c having different elevational levels. The elastic bands 20a, 20b, 20c are guided to the feeder head 53g around a guide bar 256 extending laterally across the top of the feeder head 53g. The elastic bands 20a, 20b 20c are guided through band grooves 258a, 258b, 258c defined vertically through the back of feeder head 53g.

As best shown in FIGS. 20–22, the outside elastic bands 20a and 20c are guided around vertical outer side guide surfaces 260a and 260c. The guide surfaces 260a, 260c have arcuate contours that together define a circular profile (see FIG. 22). The guide surfaces thus permit a selected constant spacing between the elastic bands 20a, 20b, 20c in a way similar to the cylindrical feeder head 53b shown in FIGS. 3–5.

As generally shown in FIGS. 17 and 18, the feeder head 53g applies the elastic bands from the three offset platforms to cooperate with an alternative elastic gripper 288. As shown in FIG. 17, outboard extending elastic regions 27g are gripped in tension by grippers 288, which are mounted at intervals along the opposing outboard edges of the conveyor drum face 32g.

The gripper 288 engages the elastic bands 20a, 20b, 20c when the feeder head 53g is moved adjacent the gripper at the outboard end of arcuate path 55g. As best shown in FIGS. 23 and 24, the gripper 288 comprises an elongate coil spring 290 that receives the bands 20a, 20b, 20c between its contracted coils. The spring is radially mounted on the drum and is extendable by an L-shaped extension rod 294. The vertical portion of the rod 294 extends axially through the coil spring and is fixed to the spring top by a fitment 297. The spring coils abut tightly against one another when the spring is not extended. The lateral portion 295 of the L-shaped rod 294 is positioned to engage the ramped upper surface of a fixed cam 292, which acts to extend spring 290, thereby producing openings between adjacent spring coils that act as holding bays to receive the elastic bands 20a, 20b, 20c at different levels.

As shown in FIGS. 17 and 23, the cam 292 is fixedly positioned adjacent the nip 34g to extend the spring before the feeder head 53g moves outside the gripper. As the gripper 288 moves by the feeder head 53g, the cam releases the rod 294 to permit retraction of the coil spring, thereby gripping the bands between the coils.

As shown in FIGS. 17, 18 and 23, a trailing row of positioning fingers 298a, 298b, 298c are fixed along the length of the edge of the conveyor face 32g to receive the elastic bands 20a, 20b, 20c. The fingers may be screws with heads to retain the individual elastic bands. The leading screw 298a has a relatively high head elevation to receive the highest elevation elastic band 20a, the intermediate screw 298b has an intermediate head level to receive intermediate band 20b, and the trailing screw 298c has a relatively low head level to receive lowest band 20c. The positioning of the screws 298a, 298b, 298c guides the bands 20a, 20b, 20c through the trailing diagonal contour portion 26g with the selected spacing between the bands.

A stationary cutting blade 300 positioned downstream of the nip 34g severs the leading bands held by the coil spring 290. The trailing elastic bands are held in tension by the retracted coil spring 290 until severed by blade 300. Another cam (not shown) is positioned adjacent a lower portion of the drum to extend the coil spring 290 so that the severed portions of the elastic bands fall from the spring 290 as scrap.

The above embodiments describe particular combinations of feeder heads 53, 53c, 53d, 53e, 53f, 53g, grippers 88, 88d, 288, and edge margin portion trimming. It is to be understood other combinations of particular feeder heads, grippers, and margin trimming treatments will work equally as well.

For instance, the grippers 88, 88d are not necessary for the use of any particular feeder head. If feeder head 53 is used without the gripper 88 and with material and a nip roller of sufficient width, a garment may be produced encasing the entire curved elastic contour and having constant spacing between the elastic bands throughout the entire curved contour. If no cutter is used, the elastic contour will extend fully up the sides of the finished garment. If a garment edge margin is trimmed away, the elastic contour will only extend along the leg openings in the finished garment.

Preferred Method

In a preferred method for applying elastic to garment material according to the invention, garment backing material 14 is moved in one direction along the flow path 16, which includes movement from bottom to top about drum 28. Prior to reaching the drum, adhesive is applied to the side of the backing material facing outward from the drum 28.

A source 39 of a plurality of elongate elastic bands 39b is provided that are guided onto the material in first and second sets, each set including a plurality, of bands 20, 22. The first and second band sets are guided from first and second positions moving symmetrically and laterally across the backing material relative to the flow path direction such that the first and second sets of elastic bands are deposited on the material in a pair of symmetric curved contours 21.

The elastic bands are deposited on the backing material adjacent the nip 34 of the drum 24 and a counter-rotating nip roller 32. The bands may be held in tension as they are so deposited. Liner material 17 may be laid over the backing material 14 and the sets of bands 20, 22 to encase the bands at the nip. The encasement step includes tightly pinching the sets of bands between the nip roller and drum.

As shown in FIGS. 1, 8, 10, 14 and 16, a selected spacing may be maintained between individual elastic bands in the first and second sets of bands 20, 22 throughout the curved contour. To provide such spacing, the individual elastic bands of the first and second sets may be guided onto the material from guide points, such as those established by cylindrical feeder head 53a. The guide points may also be outlet apertures 104 arranged along line 107 in the feeder heads 53c, 53d, 53e, 53f. The line is pivoted relative to the one direction during the lateral movement of the first and second positions.

The line may be freely pivoted by the tension in the elastic bands (FIGS. 15 and 16). Alternatively, the line may be normally biased toward a particular position, and a cam used to selectively pivot the line away from the particular position (FIGS. 8, 9, 10, and 14).

Furthermore, as shown in FIGS. 3–5, a selected spacing between the outermost bands 20a, 20c in a set may be accomplished by guiding those bands about the periphery of a feeder head 53a with a selected side-to-side dimension. Three elastic bands 20a, 20b, 20c may be deposited with constant equidistant spacing between each band where the intermediate band 20b is guided through the center of the feeder head 53a.

The method may also comprise providing material with a defined width such that the curved contour formed by the first and second sets of elastic bands extends at spaced intervals laterally outwardly beyond the edges of the material. The elastic bands so positioned outboard of the material may be gripped and held in tension prior to being severed adjacent the edge of the material.

Furthermore, the method may include the step of trimming a side margin portion of the overlaid backing and liner material.

While particular embodiments of the present invention have been illustrated and described herein, it should be obvious to those skilled in the art that variations and modifications are possible without departing from the spirit of the invention as set out in the appended claims.

What is claimed is:

1. A machine for applying elastic to material, comprising:
   a conveyor moving in one direction along a flow path and operable to carry material for garments;
   an elastic band storage for providing a plurality of elongate elastic bands; and
   an elastic feeder having a feeder head for feeding a plurality of elastic bands directly onto said material carried by the conveyor, the feeder head being movable laterally across the flow path such that the elastic bands are applied to material on the conveyor in a curved contour, the feeder head being operable to feed the elastic bands onto the material while maintaining a selected, substantially constant spacing between individual elastic bands throughout the curved contour.

2. A machine according to claim 1, wherein the feeder includes a second feeder head for feeding elastic bands onto the material, said second feeder head cooperating with the first-mentioned feeder head to deposit elastic bands on the material in a pair of symmetric curved contours.

3. A machine according to claim 1, wherein the feeder head has a defined side-to-side dimension substantially equal to the selected spacing between the elastic bands, and the elastic bands are guided around the feeder head to maintain the fixed spacing therebetween.

4. A machine according to claim 3, wherein the feeder head has a cylindrical portion about which elastic bands are guided, the central axis of the cylindrical portion extending at a substantial angle relative to the material flow path.

5. A machine according to claim 4, wherein the cylindrical portion defines a circular profile, and the feeder head has a central feeding aperture that feeds an elastic strip from the center of the circular profile, the feeder head feeding the elastic bands onto the material with a fixed spacing between individual elastic bands throughout the curved contour.

6. A machine according to claim 1, wherein the feeder head has a plurality of outlet apertures for feeding elastic bands, the outlet apertures have a fixed spacing relative to one another, and the feeder head is mounted for selected pivoting movement as it moves laterally across the flow path to produce selected spacing between individual elastic bands.

7. A machine according to claim 6, wherein the conveyor moves at a conveyor rate, the feeder head is movable across the flow path at a feeder rate that is variable between a maximum and a minimum feeder rate, and the feeder head further comprises mechanism operable to produce selected pivoting of said feeder head to different positions, the selected pivoting being related to the feeder rate.

8. A machine according to claim 7, wherein the feeder rate includes a stationary condition wherein the feeder head does not move laterally across the flow path, and the outlet apertures are arranged in the feeder head along an aperture line, the feeder head being pivoted such that the aperture line is pivoted relative to the flow path during the stationary condition at an angle=arctan (maximum feeder rate÷conveyor rate).

9. A machine according to claim 7, wherein the outlet apertures are arranged in the feeder head along an aperture line, the feeder head being pivoted such that the aperture line is oriented relative to the flow path at an angle=arctan ((maximum feeder rate−feeder rate)÷conveyor rate)).

10. A machine according to claim 6, wherein the conveyor moves at a conveyor rate, the feeder head moves across the flow path at a variable feeder rate, and the outlet apertures are arranged along an aperture line, the feeder head being pivoted such that the aperture line is pivoted relative to the flow path at an angle=arctan (feeder rate÷conveyor rate).

11. A machine according to claim 6, further comprising a cam that engages and pivots the feeder head to selected positions as the feeder head is moved laterally across the flow path.

12. A machine according to claim 6, which further comprises tensioning mechanism operable to maintain tension in the elastic bands as they are fed onto the material, and the tension of the elastic bands pivots the feeder head to maintain the fixed spacing between the elastic bands as they are applied to material.

13. A machine according to claim 6, which further comprises tensioning mechanism including a rotating nip roller with a peripheral face of the roller moving in said one direction at a speed equal to the speed of the conveyor, engaging the material on the conveyor to compress the elastic bands against the material, and maintaining selected longitudinal tension in the elastic bands being fed from the feeder head.

14. A machine according to claim 1, further comprising an elastic gripper positioned laterally outboard of the material on the conveyor, the gripper being movable in said one direction at a speed equal to the speed of the conveyor; and
   the feeder head applying elastic to the material is movable laterally to a position adjacent the gripper, allowing the gripper to receive and grasp portions of the elastic bands outboard of the material.

15. A machine according to claim 14, wherein the conveyor comprises a rotatable conveyor drum for carrying material on a peripheral drum face along the flow path, and said elastic grippers are carried by the drum adjacent opposite ends of the drum.

16. A machine according to claim 14, further comprising cutters positioned laterally outboard of the material, operable to sever the elastic bands outboard of the material after the elastic bands have been grasped by said elastic grippers.

17. A machine according to claim 16, wherein the elastic grippers releasably hold the elastic bands, the elastic grippers releasing the elastic bands after the elastic bands are severed by the cutters.

18. A machine according to claim 14, wherein said elastic gripper comprises a body defining a holding bay adapted to receive a region of the plurality of elastic bands therein, a locking member shiftable between a lock position operable to grip said region of elastic bands, an unlock position operable to release the elastic bands, and a biasing member operable to bias said locking member toward said lock position.

19. A machine according to claim 18, further comprising a cam operable to selectively shift said locking member to the unlock position to permit the elastic bands to enter said holding bay.

20. A machine according to claim 14, wherein:
the feeder head feeds the individual elastic bands from platforms having differing elevational levels; and
the gripper includes a gripper body defining a plurality of elevationally spaced holding bays adapted to receive the individual elastic bands at differing elevational levels, the gripper including a locking member shiftable between a lock position operable to close the holding bays to grip said elastic bands and an unlock position operable to release the elastic bands, and said gripper body being biased toward said lock position.

21. A machine according to claim 1, further comprising a drive cam operably connected to the feeder to move the feeder head across the conveyor.

22. A machine according to claim 1, further comprising an adhesive applicator operable to apply adhesive to secure the elastic to the material.

23. A machine for applying elastic to material, comprising:
a conveyor moving in one direction along a flow path and operable to carry material for garments;
an elastic band storage for providing a quantity of a plurality of elongate elastic bands;
an elastic feeder having a feeder head for feeding the plurality of elastic bands onto material carried by the conveyor, the feeder head being operable to feed the elastic bands directly onto the material, through a plurality of elastic outlet apertures the outlet apertures having a fixed spacing relative to one another and arranged along a line, the feeder head being pivotable about an axis adjacent the feeder head such that the line pivots relative to the flow path to feed the elastic bands onto the material with a selected, substantially constant spacing between individual elastic bands.

24. The machine according to claim 23, further comprising an elastic gripper positioned laterally outboard of the material on a second conveyor, the second conveyor movable in said one direction along the flow path at a speed equal to that of the conveyor, the feeder head moving adjacent the second conveyor such that the gripper receives and grips the elastic bands outboard of the material.

25. The machine according to claim 23, further comprising an elastic gripper positioned laterally outboard of the material on the conveyor, the gripper including positioning fingers that position the elastic bands longitudinally along a selected angle relative to the flow path.

26. A machine for applying elastic to material, comprising:
a conveyor moving in one direction along a flow path and operable to carry material for garments;
an elastic band storage for providing a plurality of elongate elastic bands; and
an elastic feeder having a feeder head for feeding a plurality of elastic bands directly onto said material carried by the conveyor, the feeder head being movable laterally across the flow path while feeding elastic bands onto the moving conveyor in a curved contour, the feeder head feeding the elastic bands with a constant perpendicular spacing between individual elastic bands through a range of feeder head and conveyor speeds has been added.

27. A machine according to claim 26, wherein the feeder head is pivotable about an axis substantially perpendicular to the flow path in order to feed the elastic with the constant perpendicular spacing between individual bands.

28. A machine according to claim 26, wherein the feeder head is pivotable through a substantial angle relative to the flow path in order to feed the elastic with the constant perpendicular spacing between individual bands.

* * * * *